(12) United States Patent
Frerichs et al.

(10) Patent No.: US 11,511,068 B2
(45) Date of Patent: Nov. 29, 2022

(54) HEAD HARNESS FOR POSITIONING A PATIENT INTERFACE

(71) Applicant: WEINMANN GERAETE FUER MEDIZIN GMBH + CO. KG, Hamburg (DE)

(72) Inventors: Arnold Frerichs, Buxtehude (DE); Martin Bechtel, Winsen/Luhe (DE)

(73) Assignee: LOEWENSTEIN MEDICAL TECHNOLOGY S.A., Luxembourg (LU)

(*) Notice: Subject to any disclaimer, the term of this patent is extended or adjusted under 35 U.S.C. 154(b) by 259 days.

(21) Appl. No.: 14/300,662

(22) Filed: Jun. 10, 2014

(65) Prior Publication Data
US 2015/0000671 A1  Jan. 1, 2015

(30) Foreign Application Priority Data

Jun. 26, 2013 (DE) .......................... 202013005712.2

(51) Int. Cl.
*A61M 16/06* (2006.01)
*A61M 16/08* (2006.01)

(52) U.S. Cl.
CPC .... *A61M 16/0683* (2013.01); *A61M 16/0633* (2014.02); *A61M 16/0825* (2014.02); *A61M 2205/6045* (2013.01); *A61M 2205/6081* (2013.01); *Y10T 29/49826* (2015.01)

(58) Field of Classification Search
CPC .......... A61M 16/0683; A61M 2207/00; A61M 2205/584; A61M 16/0633; A61M 16/0825; A61M 2205/6045; A61M 2205/6081; A61M 16/06; Y10T 29/49826; A62B 9/006
See application file for complete search history.

(56) References Cited

U.S. PATENT DOCUMENTS

| | | | | |
|---|---|---|---|---|
| 2,540,567 A * | 2/1951 | Bennett | ................. | A61M 16/06 128/206.26 |
| 6,003,213 A * | 12/1999 | Keller | ................. | A44C 5/2057 24/615 |
| 6,374,826 B1* | 4/2002 | Gunaratnam | ..... | A61M 16/0666 128/207.11 |
| 2003/0196658 A1* | 10/2003 | Ging | ..................... | A61M 16/06 128/201.22 |
| 2006/0283461 A1* | 12/2006 | Lubke | ................... | A61M 16/06 128/207.11 |
| 2007/0186931 A1 | 8/2007 | Zollinger et al. | | |
| 2010/0307502 A1* | 12/2010 | Rummery | ............. | A61M 16/06 128/205.25 |
| 2011/0247627 A1 | 10/2011 | Omura et al. | | |
| 2011/0265796 A1 | 11/2011 | Amarasinghe et al. | | |

(Continued)

FOREIGN PATENT DOCUMENTS

EP 2359888 A1 8/2011
WO 2012045127 A1 4/2012

OTHER PUBLICATIONS cpapXchange.com; 2011.*

*Primary Examiner* — Victoria Murphy
(74) *Attorney, Agent, or Firm* — Abel Schillinger, LLP

(57) ABSTRACT

Disclosed is a set of holding arrangements for a head harness in the region of a patient interface. The set comprises at least two holding arrangements which are distinguishable by identification markings and/or codings and are unambiguously assignable.

10 Claims, 5 Drawing Sheets

(56) References Cited

U.S. PATENT DOCUMENTS

2012/0285455 A1\* 11/2012 Varga .................. A61B 5/0836
                                                    128/204.21
2012/0289851 A1    11/2012 Varga et al.
2013/0220327 A1     8/2013 Barlow et al.

\* cited by examiner

HEAD HARNESS FOR POSITIONING A PATIENT INTERFACE

CROSS-REFERENCE TO RELATED APPLICATIONS

The present application claims priority under 35 U.S.C. § 119 of German Utility Model Application No. 20 2013 005 712.2, filed Jun. 26, 2013, the entire disclosure of which is expressly incorporated by reference herein.

BACKGROUND OF THE INVENTION

1. Field of the Invention

The invention relates to a head harness for positioning a patient interface on the head of a user.

2. Discussion of Background Information

Patient interfaces are used to dispense respiratory gas provided to the patient by a respirator. The patient interface is typically connected to the respirator via a respiratory gas tube and is fixed to the head of the user by means of a harness.

Since the patient interface has to be worn night after night by the patient, high requirements are imposed on the wearing comfort and fit. Similarly, high requirements are imposed on easy handling of the harness.

In addition to the precise fit of the patient interface, fastening and fixing on the head of the user are very important in order to avoid uncomfortable pressure points and leaks.

Some users have difficulties in correctly attaching their head harness to the mask again after cleaning (removal of the head harness from the therapy mask), and often the left-hand and right-hand attachment points, the top and bottom sides or even the inside and outside of the entire head harness are confused.

The head harnesses hitherto available on the market are frequently designed only for fixing the mask to the face of the user, without taking into account the wearing comfort and specifically the identification of defective fitting of the head harness at the interfaces with the mask.

It would therefore be advantageous to have available a head harness of the type set forth above such that a functional, self-explanatory application of the harness to the patient interface is provided and as a result compliance by the patient is improved.

SUMMARY OF THE INVENTION

The present invention relates to a head harness for a patient interface, which allows unambiguous and easy fitting of the head harness. In particular, the present invention provides a set of holding arrangements for a head harness in the region of a patient interface, at least two holding arrangements being provided, and at least two holding arrangements being designed differently by identification markings and/or codings and thus being unambiguously assignable.

In one aspect, the holding arrangements may be configured differently for the upper and lower halves O and U of the patient interface.

In another aspect, the holding arrangements may be configured differently for the right and left halves R and L of the patient interface.

In yet another aspect, the holding arrangement may comprise a plurality of holding elements which serve to connect a head harness to a patient interface at at least two contact points.

In a still further aspect, at least two of the holding elements may have a geometric and/or colored confusion prevention element, by means of which the assignment of the harness to the corresponding mounts in the patient interface is possible unambiguously and with no risk of confusion.

In another aspect, harness clips may be pre-fitted on the lower harness tabs of the head harness and may be connected inseparably to the textile material by end stoppers which fit over the ends of the harness tabs and may be sewn, adhesively bonded or welded there.

In another aspect, the harness clips may be pre-fitted and are connected inseparably to the textile by end stoppers which, following the pre-fitting of the harness clips, may be inserted into an orifice.

In another aspect, harness clips pre-fitted on the harness tab may be latched in the adapter on the mask body.

In another aspect, the identification marking of the harness clip and adapter may be produced by color marking or by printing of a similar type, or directly in the injection mold by raised or depressed identification marking (for example symbols, letters, numbers).

In another aspect, the identification marking of the harness clip and adapter may be produced by mechanical coding.

Alternatively, the identification marking may be produced by a similar coloring of the corresponding components consisting of harness clip and/or adapter and/or mount. Easy assignment of the harness tabs to the corresponding sides of the harness mount may be realized by coding/identification marking or by color markings or by printing of a similar type, or directly in the injection mold by raised or depressed identification markings (for example symbols, letters, numbers).

In another aspect, a color marking of the harness tabs may be produced via a colored touch-and-close fastener and/or colored seams in the same color as the corresponding side of the harness mount.

In another aspect, the touch-and-close fasteners of the head harness may be applied (sewn, adhesively bonded, welded, etc.) with an offset, directed toward the end of the harness tabs, of 10±3 mm for easier handling during the releasing and fixing of the individual harness tabs.

In another aspect, the inner and outer sides of the head harness may be configured in different colors and/or are made identifiable by an externally or internally applied overprint.

The identification marking/coding of the connecting elements between the patient interface and the head harness can thus be produced by a colored or geometric confusion prevention element, in the case of which corresponding parts are configured in an identical manner or so as to match one another and/or are the same color. According to the invention, coding of the connecting elements between the patient interface and head harness is selected for example by color coding. Coding allows the patient to find an easy assignment of the harness tabs to the corresponding mounts.

BRIEF DESCRIPTION OF THE DRAWINGS

The following drawings show exemplary embodiments of a head harness for a patient interface of the type set forth in the introductory portion. In the drawings.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
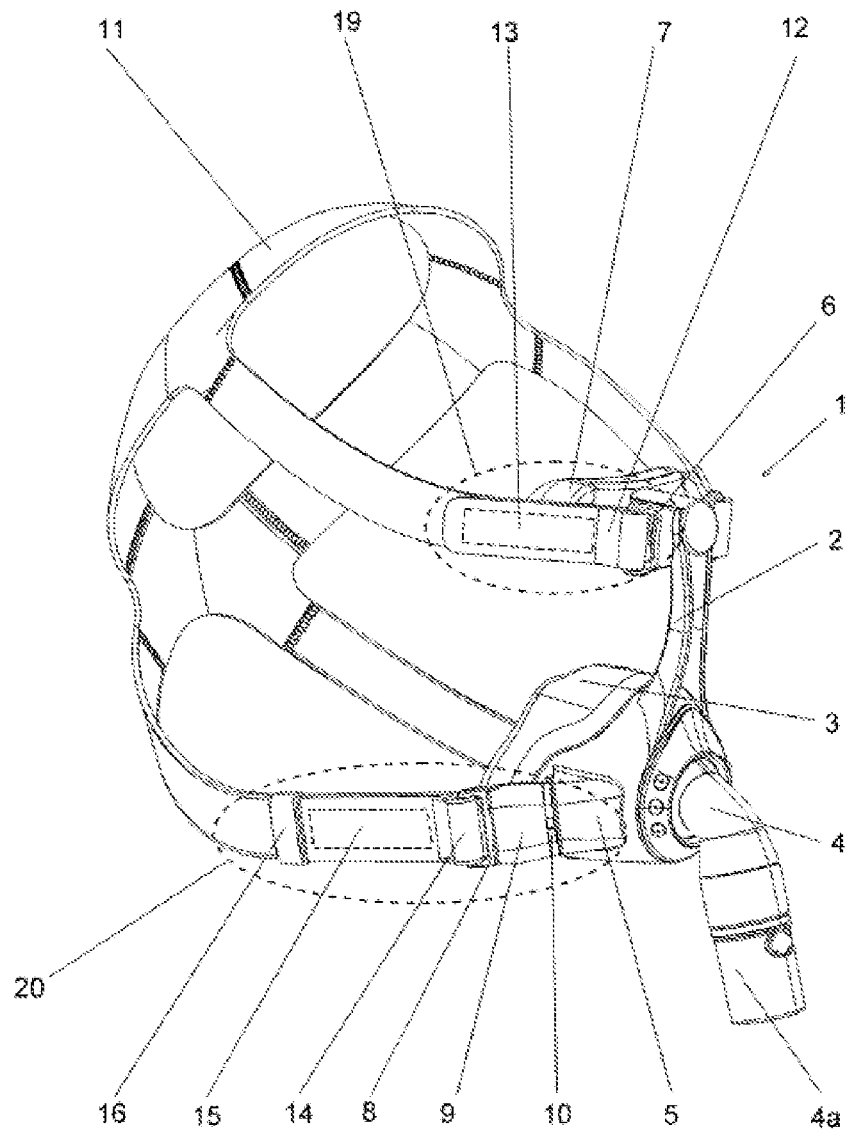
FIG. 1 shows a patient interface with harness.

FIG. 1 shows a patient interface (1) having an attached head harness (11). The patient interface (PI) has a mask body (2) at which the respiratory gas tube (not illustrated) is connected to the PI via an articulation (4) and a rotary sleeve (4a). In order to provide a seal relative to the patient's face, the mask body (2) has a sealing element (3) in the form of a mask bead having a lip seal. In order to support the patient interface (1) in the region of the patient's forehead, a forehead support (7) is used. Fixing in the region of the patient's head takes place via the head harness (11). The upper harness tabs (12) are attached to the patient interface via mounts (6) in the forehead region. The corresponding contact point is formed here by the upper harness tabs (12) which are guided through the mount (6) and are fixed by means of a touch-and-close fastener (13). The upper holding arrangement (19) created thereby thus consists of the harness tab (12), mount (6) and touch-and-close fastener (13). The upper holding arrangement (19) can be configured differently on the left-hand and right-hand sides in a side-specific manner; the left-hand upper holding arrangement (19') is identical in the present case.

The lower harness tabs (14) are fastened separately to the patient interface (1) by means of a pre-fitted harness clip (8), an actuating element (9) and an adapter (10) in mounting devices (5) in the cheek region. The lower harness tab (14) is held by means of a touch-and-close fastener (15) and fixed by the end stopper (16). This contact point thus forms a lower holding arrangement (20) consisting of the following elements: lower harness tab (14), harness clip (8), harness elements (9), adapter (10), touch-and-close fastener (15) and end stopper (16), and also mounting device (5).

On account of the different configurations of the upper holding arrangement (19) and the lower holding arrangement (20), easy and unambiguous assignment to the corresponding mounts (5 and 6) is ensured.

Figure 2:
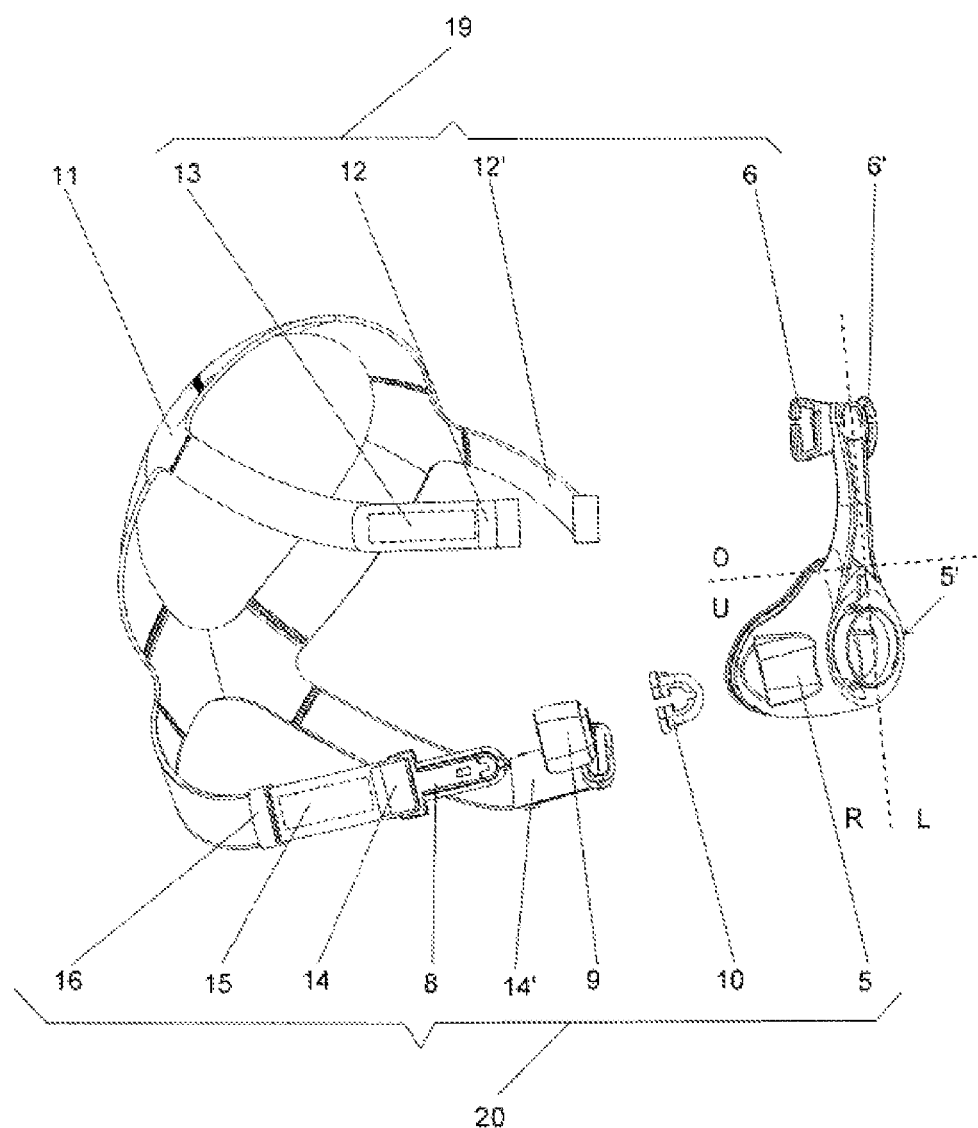
FIG. 2 is an exploded illustration, showing head harness and connection to the patient interface.

FIG. 2 shows an exploded illustration of the individual parts of the head harness and the connection to the patient interface. The head harness (11) and the patient interface are constructed in a symmetrical manner and therefore an identical left-hand (L) and right-hand (R) half are present. The connection of the head harness and patient interface is configured identically in the left-hand (L) and right-hand (R) halves at the bottom (U) (holding arrangement (20), (20')). The connection of the head harness and patient interface is likewise identical in the left-hand (L) and right-hand (R) halves at the top (O) (holding arrangement (20), (20')). However, the connection of the head harness and patient interface at the top (O) differs from the connection of the head harness and the patient interface at the bottom (U). Thus, an unambiguous geometric and/or colored confusion prevention means is provided for the upper connection (19) and the lower connection (20).

The head harness (11) is made of a haptically very comfortable material that is easily fastenable by touch-and-close fasteners and is extremely breathable. The outer cover layer consists of a loop material, and the inner layer consists of a lycra/polyester mix. The inner and outer sides of the harness (11) are configured in different colors. On the outside, an additional overprint which identifies this side as the outer side may have been applied. On the inside, the harness can additionally have a different color from the outside in order to clearly identify the inner side. On account of the small amount of material used, heat exchange via the patient's head is largely ensured, since large areas of the head, specifically the back of the head, remain uncovered. On account of the optimum course of the holding straps away from the maximum extension of the back of the head, fewer shear forces arise. The geometry of the harness allows a wide circle of patient users to be covered, since different head circumferences of about 50 to 60 cm can be covered by only one harness size. The harness is three-dimensionally preformed, and this makes it easier for the patient to assign the connecting points to the mask even in the loose state (not fitted on the mask) of the head harness. The touch-and-close fasteners (13 and 15) of the head harness (11) are applied (sewn, adhesively bonded, welded) with an offset, directed toward the harness end of the harness tabs (12, 12', 14, 14'), of 10±3 mm, and this allows the patient to easily grasp the tab (simplified handling) in order to release and fix the individual straps.

The upper harness ends (12, 12') are guided from the inside through the harness mounts (6, 6') in the region of the forehead support and fixed by way of the touch-and-close fastener (13) on the outside of the cover layer made of loop material. The harness mounts (6, 6') are slotted. This has the advantage that the patient does not have to release the harness ends (12, 12'), which are adapted to his anatomy and are fastened by way of touch-and-close fasteners, in order to remove the mask. The harness ends (12, 12') can be threaded through the slot in the harness mounts (6, 6').

Easy assignment of the upper harness tabs (12, 12') to the corresponding sides of the harness mounts (6, 6') can be produced by way of a coding/identification marking by way of color codings or by printing of a similar type, or directly in the injection mold by raised or depressed identification markings, for example symbols, letters, numbers. A color marking can be produced for example via a colored touch-and-close fastener (13) and/or colored seams which are configured in the same color as the corresponding side of the harness mounts (6, 6').

The harness clips (8) are pre-fitted to the lower harness tabs (14, 14') in the cheek region, that is to say that the harness tab is guided from the inside through the harness eye of the clip (8) and provided in each case with an end stopper (16) which fits over the end of the harness tab (14) and is sewn, adhesively bonded or welded there. The harness clips (8) are in this way connected inseparably to the textile of the harness, and this ensures unambiguous assignment of the head harness to the connecting points of the mask (here at the bottom).

The adapter (10) for the harness clip (8) is located in the mounting device (5) on the mask body (2) and is latched there in an easily pivotable manner. In order to fit the lower harness, the sliding sleeve (9) is pushed over the harness clip (8). The harness clip (8) can then be pushed in the adapter (10) and latches there by way of its snap-in hooks. Once the harness clip (8) has latched in the adapter (10), this connection cannot be released by tensile forces on the harness clip (8) but provides a secure hold. The sliding sleeve (9) serves as an actuating element for releasing the snap connection. In order to release the connection, the sliding sleeve (9) has to be pushed/pulled in the direction of the harness mount of the harness clip (8), thereby bringing about indirect deflection of the snap-in hooks of the harness clip (8) out of the adapter (10).

The holding elements (6, 12, 13) form the upper holding arrangement (19), which is configured in an identical manner on the left-hand and right-hand sides.

The holding elements (5, 8, 9, 10, 14, 15, 16) form the lower holding arrangement (20), which is configured in an identical manner on the left-hand and right-hand sides.

In order to rule out incorrect fitting, the harness clip (8) and/or sliding sleeve (9) and/or adapter (10) and/or mount (5) are marked in an identical manner. The identification marking can be produced on both sides of the mask (right and left) or on one side (right or left). This can be produced by way of a geometric and/or colored identification marking. That is to say, for example by way of color marking, by way of printing of a similar type, or directly in the injection mold by way of raised or depressed identification markings (for example symbols, letters, numbers) or by way of mechanical coding. One-sided coloring of the harness clip (8) and/or of the sliding sleeve (9) and/or of the adapter (10) in the same color is preferred. This may be realized in a translucent or opaque manner. Alternatively or in addition, the mount (5) in the for example transparently configured mask body (2) can also be provided with the same color coding as the harness clip (8) or the sliding sleeve (9) or the adapter (10).

The identification marking of the connection (20) of the harness (11) and patient interface (1) in the cheek region is thus configured in a different or identical manner on the right-hand and left-hand sides for the harness clip (8), sliding sleeve (9), adapter (10) and mount (5). In addition to the identification marking by way of color or symbols, mechanical coding between the harness clip (8) and/or adapter (10) and/or mount (5) can also be produced, the harness clip (8) and adapter (10) and/or mount (5) matching one another only in each case on the same side (right or left).

An identification marking can likewise be produced for example via a colored touch-and-close fastener (15) and/or colored seams and also an identification marking of the end stopper (16) in the same color as the corresponding harness clips (8) and adapter (10).

Thus, easy assignment of the harness ends to the corresponding connecting points to the patient interface is ensured.

Like the above-described identification marking for a 4-point harness, the same identification marking can also be produced in the case of a 2- or 3-point harness or 5-point harness.

Figure 3:
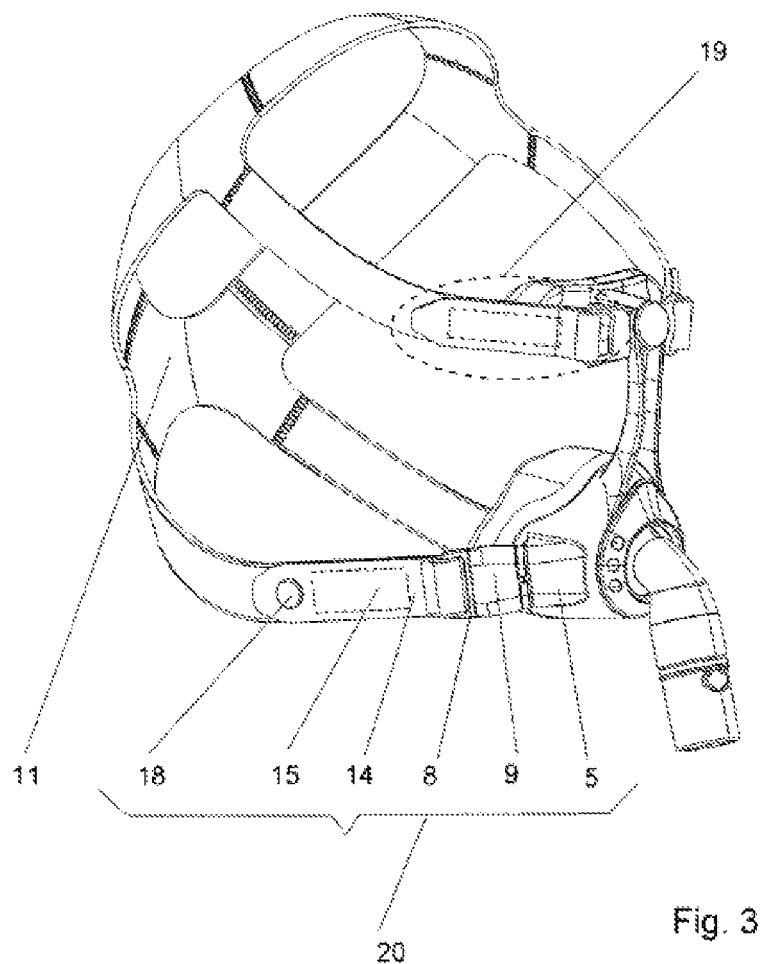
FIG. 3 shows patient interface with harness, with harness ends in the cheek region with an alternative stopper.
Figure 4:
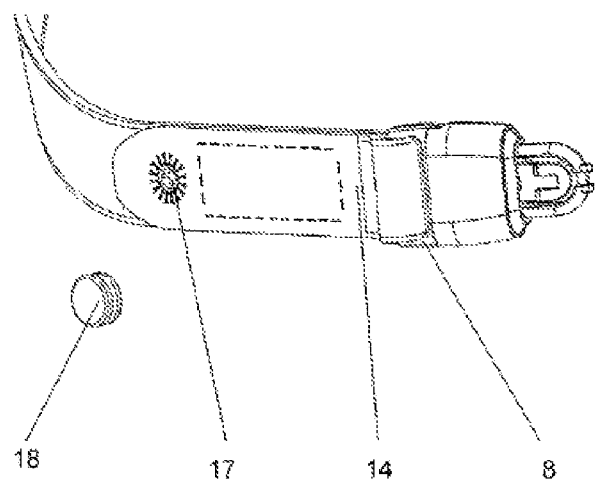
FIG. 4 shows a detail of FIG. 3, i.e., harness ends in the cheek region with an alternative stopper.

FIG. 3 and FIG. 4 show a further embodiment of the lower harness tabs in the cheek region (14) with the holding arrangement (20). The harness ends are embodied in a slightly rounded manner in this embodiment and each have an orifice (17). The orifice is reinforced by a zigzag hole seam and is located 14±2 mm from the end of the harness tabs. Following the pre-fitting of the harness clips (8), the end stoppers (18) are inserted into the orifices (17) and prevent the harness clips (8) from slipping down or being lost and likewise ensure unambiguous assignment of the head harness to the connecting points of the mask.

The touch-and-close fasteners (15) of the head harness (11) are in this case applied (sewn, adhesively bonded, welded) with an offset, directed toward the harness ends of the harness tabs (14), of 22±2 mm. The inserted end stoppers (16') in the harness tabs (14) likewise allow the patient to easily grasp the tab (simplified handling) in order to release and fix the individual straps.

Figure 5:
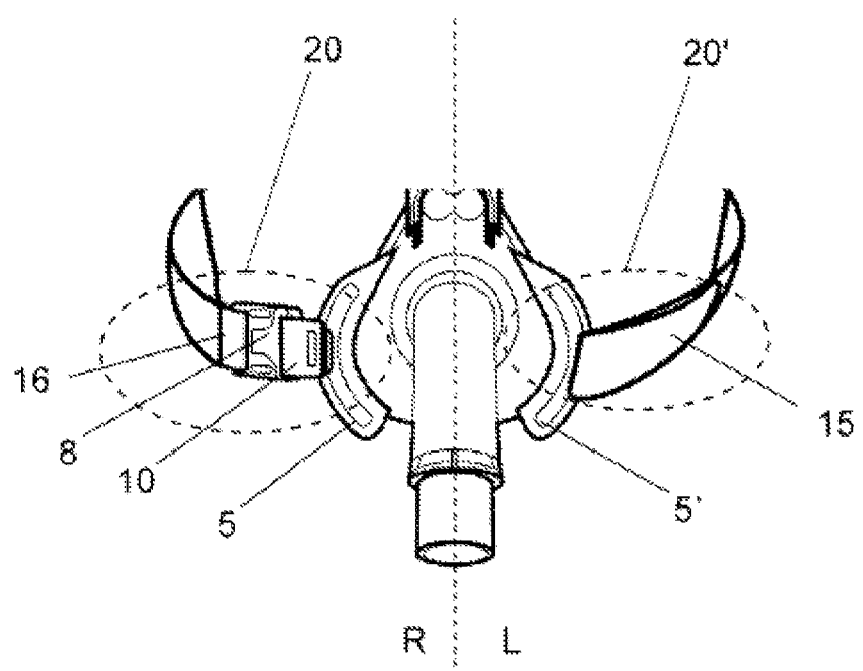
FIG. 5 shows a detail of a mask, with identical mounts on the left and right with different harness tabs.

FIG. 5 shows a patient interface with an attached head harness. The patient interface has a mask body with identical lower mounts (5, 5'). On the right-hand side (R), the holding arrangement (20) is fastened separably to the patient interface by means of a pre-fitted harness clip (8) and an adapter (10) in the mounting device (5). The inserted end stopper (16) in the harness tab (14) allows the patient to easily grasp the tab for purpose of releasing and fixing. On the left-hand side (L), the holding arrangement (20') is formed by the harness tab, which is guided from the inside through the harness mounts (5') and is fixed by way of the touch-and-close fastener (15) on the outside of the cover layer made of loop material. On account of the different configurations of the holding arrangement on the left-hand and right-hand sides, easy assignment to the corresponding mounts (5 and 5') is ensured.

The holding elements (5, 5', 8, 9, 10, 14, 14', 15, 16) form the lower holding arrangement, which is configured in different manners on the left-hand side (20) and right-hand side (20').

The patient interface is constructed in a symmetrical manner, and therefore identical left-hand (L) and right-hand (R) halves are provided. However, the connection of the head harness and patient interface in the left-hand (L) half differs from the connection of the head harness and patient interface in the right-hand (R) half. Thus, an unambiguous geometric and/or colored confusion prevention means is provided for the left-hand and the right-hand connection.

While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

LIST OF REFERENCE NUMERALS

1 Patient interface
2 Mask body
3 Sealing element
4 Tube coupling
4a Rotary sleeve
5 Mounting device for harness on mask body, right
5' Mounting device for harness on mask body, left
6 Harness-mount forehead support, right 6' Harness-mount forehead support, left
7 Forehead support
8 Harness clip
9 Sliding sleeve for harness clip
10 Adapter for harness clip
11 Head harness
12 Harness tab forehead region, right
12' Harness tab forehead region, left
13 Touch-and-close fastener
14 Harness tab cheek region, right
14' Harness tab cheek region, left
15 Touch-and-close fastener
16 End stopper
17 Orifice for end stopper
18 End stopper head
19 Holding arrangement top
19' Holding arrangement top, left
20 Holding arrangement bottom
20' Holding arrangement bottom, left

What is claimed is:

1. A set of holding arrangements for a head harness, wherein the set of holding arrangements comprises:
a head harness;
a first holding arrangement for an upper portion of a patient interface; and
a second holding arrangement for a lower portion of the patient interface;
wherein the first holding arrangement and the second holding arrangement comprise identification markings in a region of the patient interface which render the first holding arrangement distinguishable from the second holding arrangement;
wherein the first holding arrangement and the second holding arrangement are configured differently;
wherein the first holding arrangement comprises a first plurality of holding elements which serve to connect the head harness to the patient interface at two contact points and the second holding arrangement comprises a second plurality of holding elements which serve to connect the head harness to the patient interface at an additional two contact points;
wherein an adapter is located in a mounting device on the patient interface;
wherein the second plurality of holding elements comprise a harness clip, the adapter and a sliding sleeve for releasing a snap connection between the harness clip and the adapter; and
wherein the sliding sleeve brings about an indirect deflection of snap-in hooks of the harness clip.

2. The set of claim 1, wherein the first holding arrangement and the second holding arrangement are configured differently for right and left portions of the patient interface.

3. The set of claim 1, wherein the harness clip is pre-fitted on lower harness tabs of the head harness and is connected inseparably to textile material by end stoppers which fit over ends of the lower harness tabs and is at least one of sewn, adhesively bonded or welded there.

4. The set of claim 1, wherein the harness clip is pre-fitted on a harness tab, and latches in the adapter which is located in the mounting device.

5. The set of claim 1, wherein the identification markings comprise color markings on the harness clip and the adapter for the harness clip.

6. The set of claim 1, wherein the identification markings comprise raised or depressed identification markings on the harness clip and the adapter for the harness clip.

7. The set of claim 1, wherein the identification markings comprise at least one of letters and numbers.

8. The set of claim 1, wherein the identification markings comprise symbols.

9. The set of claim 1, wherein a color marking is present in the form of a colored touch-and-close fastener and/or a colored harness end and/or colored seams in a same color as a corresponding harness mount.

10. The set of claim 1, wherein the adapter is located in the mounting device in a pivotable manner.

\* \* \* \* \*